(12) United States Patent
Wollnik

(10) Patent No.: US 8,809,775 B2
(45) Date of Patent: Aug. 19, 2014

(54) CURTAIN GAS FILTER FOR HIGH-FLUX ION SOURCES

(75) Inventor: Hermann Wollnik, Sante Fe, NM (US)

(73) Assignee: Shimadzu Corporation, Kyoto-fu (JP)

( * ) Notice: Subject to any disclaimer, the term of this patent is extended or adjusted under 35 U.S.C. 154(b) by 0 days.

(21) Appl. No.: 13/816,136

(22) PCT Filed: Aug. 10, 2010

(86) PCT No.: PCT/US2010/044953
§ 371 (c)(1),
(2), (4) Date: Feb. 8, 2013

(87) PCT Pub. No.: WO2012/021124
PCT Pub. Date: Feb. 16, 2012

(65) Prior Publication Data
US 2013/0140456 A1    Jun. 6, 2013

(51) Int. Cl.
*H01J 49/00* (2006.01)
(52) U.S. Cl.
USPC ............................. 250/288; 250/281; 250/282
(58) Field of Classification Search
USPC .......................................... 250/281, 282, 288
See application file for complete search history.

(56) References Cited

U.S. PATENT DOCUMENTS

| | | | |
|---|---|---|---|
| 4,137,750 A * | 2/1979 | French et al. ................... | 73/23.2 |
| 4,821,585 A * | 4/1989 | Kempe ....................... | 73/863.23 |
| 5,175,431 A | 12/1992 | Eisele et al. | |
| 5,818,041 A * | 10/1998 | Mordehai et al. ............. | 250/281 |
| 6,653,627 B2 * | 11/2003 | Guevremont et al. ........ | 250/288 |
| 2004/0011951 A1 | 1/2004 | Giles et al. | |
| 2005/0178962 A1 | 8/2005 | Guevremont et al. | |
| 2006/0039845 A1 | 2/2006 | Messer et al. | |
| 2007/0084999 A1 * | 4/2007 | Miller et al. .................. | 250/288 |
| 2009/0294650 A1 | 12/2009 | Schneider et al. | |
| 2011/0174966 A1 * | 7/2011 | Wollnik et al. ............... | 250/286 |

FOREIGN PATENT DOCUMENTS

WO   2010/042303 A1   4/2010
WO   WO 2010042303 A1 *  4/2010

OTHER PUBLICATIONS

International Search Report of PCT/US2010/044953, dated Oct. 4, 2010.

* cited by examiner

*Primary Examiner* — Michael Maskell
(74) *Attorney, Agent, or Firm* — Sughrue Mion, PLLC

(57) ABSTRACT

A curtain-gas filter for a mass- or mobility-spectrometer that bars gases or vapors of a high-flux atmospheric pressure ion source, as we ions of high mobility and charged droplets, from entering an evacuated mass spectrometer or a mobility spectrometer that is at a lower pressure than the main filter volume of the curtain-gas filter. A portion of the ion-source buffer gas in the ion-source plume is sucked through an ion-source buffer gas inlet into the main filter volume of the curtain-gas filter, from where this ion-source gas is exhausted after a properly shaped electric field has pushed a large portion of the embedded ions into an externally provided stream of a clean buffer gas, which is sucked through a passage into a mass- or mobility-spectrometer that is at a lower pressure.

44 Claims, 8 Drawing Sheets

CURTAIN GAS FILTER FOR HIGH-FLUX ION SOURCES

BACKGROUND OF THE INVENTION

1. Technical Field

Aspects of the present invention relate to mass spectrometers, to mobility spectrometers, and to ion sources that can operate approximately at ambient pressure, and more specifically, to a "curtain-gas filter".

2. Related Art

Related art investigations of large molecules may employ mass spectrometers and mobility spectrometers. Related art mass spectrometers investigate the deflection of molecule ions in electromagnetic fields and so determine the molecule weight, which is approximately proportional to the volume of the molecule under investigation. Related art mobility spectrometers investigate the speed of an ion when dragged through a buffer gas, a quantity which is approximately proportional to the cross section of the molecule under investigation.

For the related art systems, selection of the ion source is important. Commonly used ion sources for large molecules include "electrospray ion sources (ESI)" as disclosed in J. B. Fenn, JASM 4 (1993) 524 and sources for "matrix assisted laser desorbed ion sources (MALDI)" as disclosed in M. Karas, F. Hillenkamp, Anal. Chemistry 60 (1988) 2299 as well as sources for "electrospray-assisted laser desorbed ion sources (ELDI)" as disclosed in M. Z. Huang, H. J. Hsu, J. Y. Lee, J. Jeng, J. Shiea, J. Prot. Res. 5 (2006) 1107, or "desorption electrospray-ion sources (DESI)" as disclosed in Z. Takats, J. M. Wiseman, B. Gologan, G. Cooks Science 306 (2004) 471. These sources may be used at elevated pressures, including at atmospheric pressure. However, other related art ionization methods in other "atmospheric pressure ion sources (API)" can be used as well.

Related art investigations of molecules have become important in applications related to biology, medicine and pharmacology. These related art techniques allow characterization of a molecule not only by weight and cross section but also by structure, which becomes apparent by investigating the fragments into which a molecule will break when it absorbs energy, for example, by collisions with buffer gas molecules or atoms.

A curtain gas filter that operates with low flux ion sources is disclosed in U.S. patent application No. 61/103,168 and International Application no. PCT/US2009/057281, which are each incorporated herein in their entirety by reference.

SUMMARY OF THE INVENTION

Aspects of the exemplary, non-limiting embodiments include a "curtain-gas filter" for mobility- and/or mass-analyzers that allows molecule ions to enter these analyzers, but that keeps out ion-source gases and vapors as well as ions whose mobilities are outside of a range of mobilities with the lower end of this range being adjustable by potentials applied to at least one electrode of the "curtain-gas filter". Into a "curtain-gas filter", as described in greater detail below, "ion-source buffer gas" is sucked through an "ion-source buffer gas inlet" from the "plume" of the "ion-source buffer gas" into the "filter volume", i.e. the main filter volume of the "curtain-gas filter", placed before a passage through which ion containing buffer gas is sucked from the main filter volume into a low pressure mobility- and/or mass-analyzer. In this arrangement, the whole body of the "curtain-gas filter" or parts of it and/or the "ion-source buffer gas inlet" is optionally heated.

In detail, the ion containing buffer gas is sucked into the mentioned passage only from a portion of the main filter volume, i.e. from the so called "ion extraction volume". This "ion extraction volume" is filled by an externally supplied "clean buffer gas" so that no gases or vapors of the ion-source buffer gas can enter the mobility- and/or mass analyzer in which case, however, no ions can enter unless the ions have been transported with the "ion-source buffer gas" into the main filter volume, and there, existing electric fields push a portion of these ions into the flow of the "clean buffer gas" or into the "ion extraction volume" directly. For any given strength of this electric field:

high-mass low-mobility ions are sucked from the "ion-source buffer gas" flow into the "clean buffer gas" flow while low-mass high-mobility ions will be pulled through the "clean buffer gas" flow to an electrode where they will be neutralized and thus eliminated, while very high-mass ions of very low-mobilities are only partially pulled into the flow of the "clean buffer gas".

The "curtain-gas filter" thus acts as band-pass mobility-filter having a selection range that varies with the magnitude of the mentioned electric field. This "curtain-gas filter" may achieve the following:

1. Allow operation of a mass- and/or mobility analyzer with a "clean buffer gas" of which the temperature, humidity and purity can be controlled. While retaining most of the ions of interest, this "curtain-gas filter" substantially eliminates ion-source buffer gases and vapors originating from a gas- or liquid-chromatograph, residues of solvents or of materials of matrices into which the molecules of interest had been embedded. As a consequence, this "curtain-gas filter" avoids the formation of surface layers on electrodes and surfaces inside mobility- and/or mass analyzers.

2. Effectively use so-called "shift agents", which when added to the sample material that is fed to an ion source may react with the molecular ions of interest. Thus, the mass spectrum can show new mass lines, though when a mobility analyzer is used as an ion-prefilter, it may be necessary to change the settings of the mobility analyzer which may require recording a number of mass spectra. When using a "curtain-gas filter" according to the exemplary embodiments, such "shift agents" can be added to the "clean buffer gas" in which case:

2.1 The "shift reagents" can react chemically with an already mobility-analyzed molecular ion or can attach themselves to such a molecular ion. In this case, thus, the settings of the mobility analyzer are identical to the case when no "shift reagents" were added to the "clean buffer gas".

2.2 The "shift reagents" can be added either continuously or only during short time intervals, in which case the chemical reactions or the attachments occur only during these short time intervals so that only during these time intervals the so formed molecular ions can be recorded. Accordingly, the corresponding molecules can be recorded with high sensitivity.

3. Ions of low-masses and high-mobilities like water and/or solvent clusters may be substantially eliminated by adjusting the shape and magnitude of the electric fields in the "curtain-gas filter" so that only ions of high-masses and low-mobilities, which are more subject to gas-flow forces, are pushed into the "clean buffer gas" flow and/or into the "ion extraction volume".

3.1 By comparing mass spectra recorded of ions whose mobilities are higher than specific but different mobility thresholds, one may gain additional insight into the molecule composition.

3.2 By guiding the effluent of a gas- or liquid-chromatograph into an ion source and establishing in a "curtain-gas filter" a mobility elimination threshold that is high enough to substantially eliminate protonated water and solvent clusters, the total ion current downstream of the "curtain-gas filter" of the exemplary embodiment contains only ions of molecules of interest. Monitoring this total ion current as a function of time, one thus monitors with high sensitivity the appearance of chromatographically separated molecules.

4. In case of an "electrospray ion source (ESI)" or a "droplet pickup ion source", for instance ELDI or DESI, charged droplets exist that transfer their charges to incorporated molecules of interest when the liquid of these droplets evaporates. This process may be incomplete when the ions enter the passage, i.e. the at least one capillary and/or the at least one diaphragm that allows the buffer gas to enter the mobility- and/or mass-spectrometer. In case of the exemplary "curtain-gas filter" is used as a prefilter for mobility- and mass-analyzers, mainly molecule ions with or without adducts are pushed by electric fields into the gas flow of the "clean buffer gas" and/or the "ion extraction volume", while large droplets stay in the "ion-source buffer gas" and cannot enter the mobility- and/or mass-analyzer.

Molecules with a low affinity to the droplet surfaces as disclosed in N. B. Cech, C. G. Enke, Mass Spectr. Rev. 20 (2001) 362, a property that relates to the solubility of the molecules under consideration, are only released at the end of the droplet evaporation process. Consequently, such ions are not recorded in a sequentially arranged mobility-analyzer and/or mass-analyzer, unless measures are taken to evaporate the liquid of the droplets in a so-called desolvation region or during their transport from the ion source to the ion extraction volume, such as the heating of surfaces in the "curtain-gas filter". By keeping the temperatures of the "curtain gas filter" low and excluding large charged droplets from entering the mass-analyzer or the mobility-analyzer, highly soluble ions thus can be reduced or substantially eliminated. The level of reduction or elimination can be varied with varied temperatures of the "curtain gas filter", thus providing additional insight into the structure of the molecules under consideration.

Alternatively, a reagent may be added that changes the surface affinity of the molecules of interest in a charged droplet, and that causes ionized molecules to be released earlier than if the reagent is not added. This "shift reagent" may be added either to the sample that is fed to an electrospray ion source or to the "clean buffer gas" of a "curtain-gas filter" according to exemplary embodiments in which case the "shift reagent" would react with mobility selected ions only.

According to an exemplary embodiment, a spectrometry system includes an ion source that produces an ion containing ion-source plume, an "ion-source buffer-gas" inlet configured to receive ion containing "ion-source buffer gas" from the ion-source plume, and a clean buffer-gas inlet configured to receive a clean buffer gas from an external source. Further, a curtain-gas filter is provided that includes a first low-turbulence gas guide that transfers the "ion-source buffer gas" as a substantially laminar gas flow from the "ion-source buffer gas" inlet to a main filter volume, i.e. a main filter volume of the "curtain-gas filter" having a gas pressure lower than a gas pressure of the ion-source plume, a second low-turbulence gas guide that transfers the "clean buffer gas" as a substantially laminar gas flow from the "clean buffer gas" inlet to the main filter volume, and a passage positioned between an "ion extraction volume" within the main filter volume and a spectrometer having a gas pressure lower than the gas pressure in the main filter volume. Additionally, potentials applied to at least two electrodes generate an electric field to push ions having a range of mobilities from the "ion-source buffer gas" in the main filter volume into the "clean buffer gas" in the main filter volume or directly into an "ion extraction volume", i.e. that part of the main filter volume that is closest to the passage, to generate an ion containing "clean buffer gas" in the "ion extraction volume" and outside of the "ion extraction volume" but within the main filter volume an ion-depleted "ion-source buffer gas". The main filter volume includes the "ion-source buffer gas" and the "clean buffer gas" as substantially unmixed flows having a boundary therebetween, and at the end ion-containing "clean buffer gas" in the ion extraction volume flows substantially through the passage into the spectrometer, and any remaining gas in the main filter volume outside of the "ion extraction volume" is exhausted. The spectrometer is a mass spectrometer or a mobility spectrometer, or both.

According to another exemplary embodiment, the ion source blows its plume into either a region of ambient pressure or a vessel in which the gas pressure is between approximately 20 mbar and several bar.

According to yet another exemplary embodiment, the passage is at least one of a capillary and a diaphragm of circular, elliptical or polygonal bore that guides the ion containing clean buffer gas from the ion extraction volume into the spectrometer. The passage may further include a guide tube of circular, elliptical or polygonal bore that transports the ion-containing clean buffer gas from the "ion extraction volume", through the at least one of the capillary and the diaphragm, and into the spectrometer wherein different potentials may be applied to the guide tube as compared with the at least one of the capillary and the diaphragm. The bores of the capillary, of the guide tube and of an inner tubular electrode and an outer tubular electrode, both placed substantially coaxial around the passage have cross sections that are constant or varied over parts of their respective lengths. The capillary may be shaped to have a form of a Lavall Nozzle whose bore first decreases and then increases.

According to still another exemplary embodiment, the first low-turbulence gas guide and the second low-turbulence gas guide each include a ring canal and an annular region formed (a) between the inner tubular electrode and the outer tubular electrode for the first low-turbulence gas guide and (b) between the passage and the inner tubular electrode for the second low-turbulence gas guide. These ring canals are either part of the respective annular regions or are connected to them via a number of openings in the walls of the ring canals wherein the walls of the annular regions have smooth surfaces and their cross sections may decrease over at least parts of their lengths to ensure laminar gas flow. Further the "ion-source buffer-gas" and the "clean buffer-gas" each flow through the respective annular regions of the first low-turbulence gas guide and of the second low-turbulence gas guide substantially parallel to the axis of the passage, and opposite to the gas flow direction of the passage.

According to another exemplary embodiment, the first low-turbulence gas guide and the second low-turbulence gas guide may each include a ring canal and an annular region formed between plates arranged in the plane of the ring canals wherein the "ion-source buffer-gas" and the "clean buffer-gas" flow radially between the plates to the passage, wherein an axis of the passage is substantially perpendicular to the planes of the ring canals.

According to yet another exemplary embodiment, the passage may be formed from insulating or high resistivity material having (a) an inner surface coated by a conductive or resistive material or (b) parts made of conductive or resistive materials through which a current may be passed. The spectrometry system may also include a substantially cylindrical electrode placed within the guide tube so as to permit application of a static and/or alternating voltage therebetween, wherein axes of the guide tube and the substantially cylindrical electrode are parallel or coinciding. Also the outer tubular electrode in the first low-turbulence gas guide may be divided longitudinally so as to permit application of a static and/or alternating voltage between the inner tubular electrode and a section of the divided outer tubular electrode. In both cases radial fields are formed that deflect high mobility ions embedded in the gas streams that moves through the respective fields. The alternating voltage may be a high frequency voltage that has an asymmetric wave form comprising a train of substantially rectangular positive and negative pulses with the positive pulses having different amplitudes and durations than the negative pulse and wherein an absolute value of an integral over the positive pulses is substantially equal to an absolute value of an integral over the negative pulses. An adjustable and/or scanned DC voltage may also be added to the train of positive and negative pulses. Further, the train may be generated by a high voltage switch and applied either directly as a train of high quality rectangular pulses or through a transformer as a train of more sinusoidal pulses to the substantially cylindrical electrode or the section of the outer tubular electrode of the first low-turbulence gas guide.

According to still another exemplary embodiment, an end of the passage is either substantially flush with or extends deeper into the main filter volume beyond the inner tubular electrode or the outer tubular electrode or a surrounding flat ring electrode. Further, at least one of the inner tubular electrode, the outer tubular electrode and the surrounding flat ring electrode is divided azimuthally or in case of the inner or the outer tubular electrode longitudinally into at least two parts to which different potentials are applied.

According to a further exemplary embodiment, the passage itself and/or at least one of the surrounding tubular electrode and/or at least one of the surrounding flat ring electrode are replaced by at least two substantially planar electrodes that are either substantially parallel to the axis of the passage or that are substantially symmetric and inclined relative to the axis of the passage and wherein different potentials may be applied to the at least two substantially flat plates.

According to another exemplary embodiment, the main filter volume of the curtain-gas filter is defined on one side by the end of the passage and by the inner tubular electrode which is part of the first and second low-turbulence gas guides, and is defined on the other side by at least one repeller whose axis is parallel to or coinciding with the axis of the passage wherein the electric field in the main filter volume is formed by applying to the at least one repeller electrode equal or different ion repelling potentials measured relative to the potential of the gas intake part of the passage and/or by applying to the "inner tubular electrode" and/or the "outer tubular electrode" the same or different potentials than to the passage. Additionally, a tubular ring electrode is arranged substantially proximal to the at least one repeller and placed substantially around the "main filter volume" with the axis of the tubular ring electrode being substantially parallel to or coinciding with the axis of the passage wherein the ring electrode may be subdivided into at least two sections and wherein to these subelectrodes equal or different ion repelling potentials may be applied. This tubular ring electrode may be part of the divided "outer tubular electrode".

According to yet another exemplary embodiment, the at least one ion-source buffer gas inlet and/or the at least one clean buffer gas inlet are arranged substantially radial and/or substantially tangential to an ion-source buffer gas ring canal or to a clean buffer gas ring canal. Further, the ion-source buffer gas ring canal and/or the clean buffer gas ring canal are either part of the respective annular regions or have in their walls a number of azimuthally arranged openings through which gases can stream into the respective annular regions.

According to still another exemplary embodiment, the curtain-gas filter is mounted in a vessel in which the at least one ion source produces the at least one ion-source plume at an elevated gas pressure maintained by controlling the pressure of the ion source, and wherein the pressure of the external clean gas supply is adjusted so that the clean gas flow into the main filter volume of the curtain-gas filter exceeds the flow from the main filter volume through the passage.

According to an additional exemplary embodiment, the gas pressure in the at least one ion-source plume is at ambient pressure and a pump reduces the pressure in the main filter volume to a pressure that is lower than the pressure in the at least one ion-source plume, wherein the pump exhausts gas from the main filter volume, and wherein the pressure of the external clean gas supply is adjusted so that the clean gas flow into the main filter volume of the curtain-gas filter exceeds the flow from the main filter volume through the passage.

According to a further exemplary embodiment, the bore of at least one of the at least one ion-source buffer gas inlet is of substantially round, elliptical or polygonal cross section and increases or decreases its diameter for at least a portion of its length.

According to yet another exemplary embodiment around and/or at some distance to a gas intake part of at least one of the at least one ion-source buffer gas inlet an ion concentrator is arranged that includes consists of electrodes made of conductive or resistive gridded or solid material with ion repelling potentials being applied to these electrodes so that the formed electric field approximates one that would be obtained by an ion attracting point-charge placed approximately in the middle of the gas intake of at least one of the at least one ion-source buffer gas inlet. This ion concentrator comprises at least one of (a) at least one tubular electrode or circular, elliptical, or polygonal cross-section whose axes substantially coincide with the axis of the plume or of at least one of the least one ion-source gas inlet, (b) at least one planar ring electrode of circular, elliptical or polygonal area whose axis passes substantially through a point located in the middle of the gas intake part of at least one of the at least one ion-source buffer gas inlet and whose plane substantially includes that point from which the at least one in source plume seems to originate, (c) a grid that approximates a sphere whose center is located approximately in the middle of the gas intake part of at least one of the at least one ion-source buffer gas inlets, and (d) an electrode that approximates the form of at least one half-cylinder whose axes pass substantially through a point located approximately in the middle of the gas intake part of at least one of the at least one ion-source buffer gas inlet. Each of the electrodes of the ion concentrator may be divided into at least two parts to which different potentials may be applied. Further, at least one of the at least one planar ring electrode may be formed as a printed circuit board. Also, the axis of least one of the electrodes that approximate the form of a half-cylinder may be tilted with respect to the axes of other electrodes that approximate the form of a half-cylinder.

According to another exemplary embodiment, electrodes of round, elliptical or polygonal cross section are arranged around a part of the at least one ion source plume wherein the axes of these electrodes are straight or curved. Also these electrodes are split into at least two parts to which equal or different potentials DC- and/or AC-potentials are applied. One of the ion extracting and beam forming electrodes closest to the ion source is at a potential close to that of the ion source. Further, at least one of these electrodes may be heated so as to assist the desolvation of droplets in the at least one ion source plume.

According to another exemplary embodiment, at least one of a purity, a pressure, a temperature, and a humidity of the externally supplied clean buffer gas or the ion-source buffer gas in the ion-source plume is controlled, kept constant or varied over time.

According to still another exemplary embodiment, to the clean buffer gas a shift reagent is added which either reacts chemically with mobility selected molecule ions or that becomes an adduct to the mobility selected molecule ions so that the resulting ion has a different mass than the original molecule ion. The shift reagent is added intermittently for short periods, so that the molecules of larger or smaller masses or of larger or smaller mobilities appear only for short periods in the recorded spectra of the spectrometer.

BRIEF DESCRIPTION OF THE DRAWINGS

The above and/or other aspects and features will become apparent and more readily appreciated from the following description of the exemplary embodiments, taken in conjunction with the accompanying drawings, in which.

DETAILED DESCRIPTION OF THE INVENTION

Figure 1:
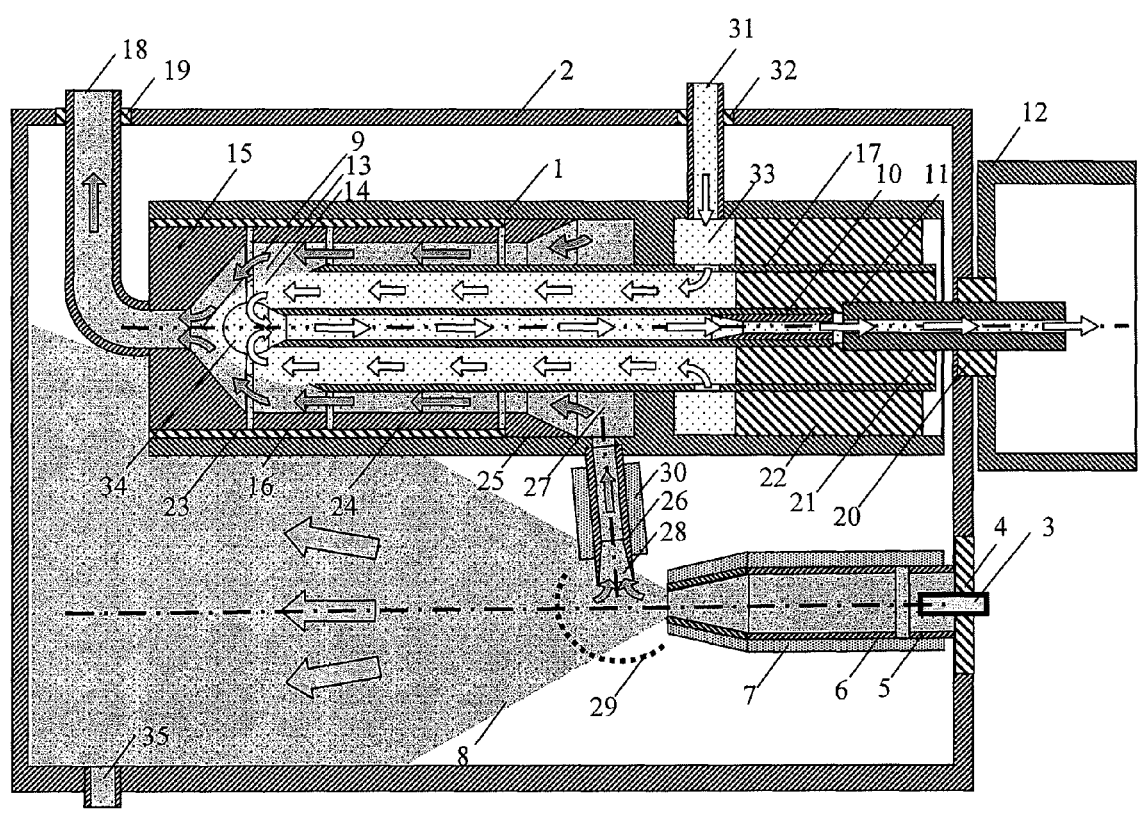
FIG. 1 is a schematic view of a first exemplary, non-limiting embodiment of a "filter for mass- and mobility-analyzers"

Exemplary embodiments will be described in greater detail with reference to the accompanying drawings. In the following description, the same drawing reference numerals are used for the same elements in all drawings. The matters defined in the description such as a detailed construction and arrangement of elements are only those provided to assist in a comprehensive understanding of the invention. Thus, it is apparent that the present invention can be carried out without being limited to those defined matters. Also, well-known functions or constructions are not described in detail since they would obscure the invention in unnecessary detail.

FIG. 1 is a schematic view of a first exemplary, non-limiting embodiment of a "curtain-gas filter" for mobility- and mass-analyzers that substantially eliminates ion-source buffer gases and vapors as well as molecule ions of very high and very low mobilities and of undesolvated charged droplets. The "curtain-gas filter" is contained in an enclosure 1 housed in a vessel 2 that also contains an ion source 3, held in place by an insulator 4. In an exemplary embodiment, the ion source 3 is a high pressure ion source that operates at a gas pressure between 20 mbar and several bar. This ion source 3 blows its "ion-source buffer-gas" together with embedded ions through a region in which ion extraction and beam formation electrodes 5, 6 are placed to which different potentials are applied and which when heated by a heater 7 act as hot walls of a "desolvation chamber" having a gas pressure that is lower than that of the ion source 3, and higher than that in the vessel 2. When an electro-spray ion source is used, this "desolvation chamber" may enhance the evaporation of the liquid of charged droplets having a charge that is finally left at individual atoms and molecules originally contained in the droplets.

When leaving this "desolvation chamber" the "ion-source buffer-gas" forms a diverging ion-containing plume 8 in the vessel 2 as is indicated by three arrows. The axis of this plume 8 is shown to be substantially parallel to the axis of the curtain-gas filter. However, the two axes could also form an angle with respect to each other.

From this plume 8, the ions must be passed into the filter volume 9, i.e. the main filter volume of the curtain-gas filter in which the gas pressure is lower than that in the vessel 2 and from there through a passage, i.e. the guide tube 10 and the capillary 11, into at least one of a mass-spectrometer and a mobility-spectrometer (both not shown) housed in a vessel 12 in which a gas pressure exists that is even lower than the gas pressure in the main filter volume 9. Besides the ion-containing "ion-source buffer gas" 13 of the plume 8 also an externally supplied "clean buffer gas" 14 is passed into the filter volume 9 of the curtain-gas filter wherein both gas flows are substantially unmixed, having a boundary therebetween.

Within this filter volume 9, electric fields push ions from the flow of the "ion-source buffer gas" 13 into the flow of the "clean buffer gas" 14 as well as directly into an ion extraction volume 34 within the filter volume 9 from where ions are passed into the passage, i.e. the guide tube 10 and the capillary 11. These electric fields are formed by applying ion repelling potentials to at least one flat or substantially conical "repeller" 15 and to at least one substantially tubular electrode 16 positioned substantially around the filter volume while applying ion attracting potentials to the guide tube 10 and to an "inner tubular electrode" 17. This largest part of the "clean buffer gas" that now contains ions is then substantially sucked through the passage, i.e. the guide tube 10 and the capillary 11, into the vessel 12 while the ion depleted "ion-source buffer gas" and a small portion of the clean buffer-gas are substantially exhausted through an exhaust canal 18 held in place by an insulator 19.

In this electric field ions of very high mobility will substantially be pulled to the ends of the guide tube 10 and the "inner tubular electrode" 17, and there be neutralized while ions of lower mobility, which are more subject to gas-flow forces, will be pushed substantially into the flow of the "clean buffer gas" through the passage, though ions of very low mobility which are mainly subject to gas-flow forces will not even leave the "ion-source buffer gas flow" and be exhausted.

The bores of the passage, i.e. the bores of the guide tube 10 and of the capillary 11 may have circular, elliptical or polygonal cross sections wherein the magnitude of these cross sections may vary for at least part of the lengths of the guide tube 10 and the capillary 11. Also the guide tube and/or the capillary 11 may be shaped so as to have a form of a Lavall Nozzle in which the bore of the capillary first decreases and then increases. Further yet the guide tube 10 as well as the capillary 11 may be built of insulating or high resistivity material with (a) their bores being coated by a conductive layer or by a resistive layer through which a current may be passed or (b) comprise parts made of conductive or of resistive materials through which a current may be passed.

Further, the guide tube 10 extends further into the filter volume 9 than the "inner tubular electrode" 17. Between the tubes 10 and 17, an additional tubular electrode (not shown) may be placed to which a high ion attracting potential is applied. Further, insulators 20, 21 and a spacer 22 hold the guide tube 10 and the capillary 11 in place, and an insulator 23 holds the at least one repeller 15 and the "outer tubular electrode" in place with this "outer tubular electrode" being divided into tubular electrodes 16, 24 and 25 to which equal or different potentials may be applied.

In the exemplary embodiment of FIG. 1, two gas flows are guided into the filter volume 9:

A. The flow of the "ion-source buffer gas" 13 is passed into the filter volume 9 after being received from the ion source plume 8 by at least one inlet 26, here referred to as "ion-source buffer gas inlet", through a first low-turbulence gas guide that comprises a ring canal 27 and an annular region between two tubes that are both substantially coaxial to the guide tube 10 and the capillary 11, i.e. the "inner tubular electrode" 17 and an "outer tube" segmented into parts 16, 24, 25. More specifically, the ion-source buffer-gas is passed from the ion-source plume 8 through the ion-source buffer-gas 26 inlet into the ring canal 27 and from there through a number of azimuthally arranged openings into said annular region. Heating at least parts of the "curtain-gas filter", this first low-turbulence gas guide acts as a desolvation chamber to neutral and charged droplets that may have entered the "curtain-gas filter" with the "ion-source buffer gas". Also the "ion-source buffer gas inlet" may act as a "desolvation region" if its temperature is elevated by a heater 30. These desolvation regions will cause most leftover charged droplets of the sucked in ion-source buffer gas to evaporate, in which process the droplet charges are substantially transferred to atoms or molecules initially dissolved in the liquid of the droplets. To enhance the flow of ions and small charged droplets in the plume 8 towards the gas intake part 28 of the at least one "ion-source buffer gas inlet", a shaped grid 29 is placed at an ion repelling potential.

B. The flow of a "clean buffer gas" 14 is passed into the filter volume 9 after being received from an external source by at least one inlet 31, here referred to as a "clean buffer gas inlet", held in place by an insulator 32, and then into the filter volume 9 through a second low turbulence gas guide that comprises a ring canal 33 and an annular region between the guide tube 10 and the "inner tubular electrode" 17. More specifically, the clean buffer-gas flow passes through the ion-source buffer-gas inlet 31 into the ring canal 27 and from there through a number of azimuthally arranged openings into said annular region. In the filter volume 9 a portion of the ions embedded initially in the "ion-source buffer gas" is pushed by electric fields into the "clean buffer gas" with the main portion of this ion containing "clean buffer gas" being sucked through the guide tube 10 and the capillary 11 into the vessel 12, while the rest of the "clean buffer gas" is released through the exhaust canal 18 together with the ion depleted "ion-source buffer gas". This ion containing "clean buffer gas" is sucked into the vessel 12 substantially only from the "ion extraction region" 34 which is a portion of the main filter volume 9. Optionally the guide tube 10 can be omitted if a longer capillary 11 is used, which would extend from the vessel 12 into the filter volume 9.

For these two gas flows to occur, the gas pressure in the ion-source plume 8 must be higher than the gas pressure in the filter volume 9, which in turn must be higher than the pressure outside the vessel 2, while the gas pressure in the vessel 12 must be substantially lower than that in the main filter volume 9. These pressure differences are established by controlling the gas pressure in the ion source 3 and the conductance of the "desolvation chamber" formed by the tubular electrodes 5, 6 as well as the conductance of the drain 35 in the vessel 2, and by limiting the cross section of the first low-turbulence gas guide. i.e. the cross section of the annular region formed region between the "inner tubular electrode" 17 and the "outer tubular electrode" divided into tubular electrodes 16, 24, 25. Furthermore the gas pressure in the external clean gas supply must be adjusted so that the clean gas flow into the filter volume of the curtain-gas filter slightly exceeds the flow from the filter volume through the passage in which case the ion depleted ion-source buffer gas will pass through the exhaust canal together with a small portion of the clean buffer gas.

As can be seen in FIG. 1, the flow of the ion-source buffer gas through the annular region of the first low turbulence gas guide and the flow of the clean buffer gas through the annular region of the second low turbulence gas guide are opposite to the direction of the gas flow through the passage.

To achieve substantially laminar gas flows of the ion-source buffer gas and of the clean buffer gas within the filter volume 9 and into the ion extraction volume the walls in the low-turbulence gas guides must be very smooth, i.e. the walls of the ring canals 27 and 31 and the walls of the corresponding annular regions, i.e. the outer surfaces of the guide tube 10 and of the capillary 11 as well as the inner surfaces of the tubular electrodes 16, 24, 25 but also the inner and the outer surfaces of the "inner tubular electrode" 17 must be very smooth. Furthermore the walls of the tubes 10 and 17 may be very thin and their ends in the filter volume 9 may be chamfered as is shown in FIG. 1. The same holds for the gas intake of the at least one "ion-source buffer gas" 26.

The at least one "ion-source buffer gas inlet" 26 is shown as being straight, though it could as well be curved. Also the axis of the gas intake part 28 of the at least one "ion-source buffer gas inlet" 26 and the axis of the passage, i.e. the tube 10 and the capillary 11, are shown as being substantially parallel to each other, though any other angle could have been chosen as well. In addition to the foregoing exemplary embodiment disclosed with respect to FIG. 1, another exemplary geometry involves arranging the axis of the ion source 3 and of the plume 8 to be inclined or substantially perpendicular to the drawing plane of FIG. 1.

In the exemplary embodiment shown in FIG. 1, ions of high mobilities can be substantially eliminated not only by pushing them by the potentials of the at least one repeller 15 and the at least one tube segment 16 towards the ends of the guide tube 10 and/or of the "inner tubular electrode" 17, but also by applying a constant or a varying voltage between the inner tubular electrode 17 and the at least one tube segment 24. The resulting radial electric field and the longitudinal gas flow in the annular region between the inner tubular electrode 17 and the at least one tube segment 24 then acts as a "differential mobility analyzer (DMA)" as disclosed in E. O. Knutson, K. T. Whitby, J. Aerosol Science 6 (1975) 443, in which ions of high mobilities are pushed to the electrode walls where they are annealed. By varying this voltage, one may also shift the "cutoff threshold" of high-mobility ions.

Adding a high-frequency voltage of an asymmetric waveform between the inner tubular electrode 17 and the tube segment 24, one creates a situation as in a differential mobility FAIMS system, as disclosed in B. M. Kolakowski, Z. Mester, Analyst 132 (2007) 842, in which the nonlinear dependence of the mobility of ions on a magnitude of an electric deflecting field is used to allow at a given time only ions to pass for which the ratio of their high-voltage mobility, and their low-voltage mobility has a determined value. The high-frequency voltage that has an asymmetric wave form may include a train of substantially rectangular positive and negative voltage pulses that are applied directly between the inner tubular electrode 17 and the at least one tube segment 24 by a high voltage switch as disclosed in U.S. patent application Ser. No. 11/812,886, having a filing date of Jun. 22, 2007, which is incorporated herein by reference in its entirety. However, the train of substantially rectangular positive and negative voltage pulses may also be applied through a transformer. This will increase the pulse amplitudes but reduce their rectangularity especially for the short pulses which reduces the achievable performance of the mobility analyzer, though a so reduced separation power may still be acceptable for certain applications. For example but not by way of limitation, also an adjustable and/or scanned DC voltage may be added to the train of positive and negative pulses.

Figure 2:
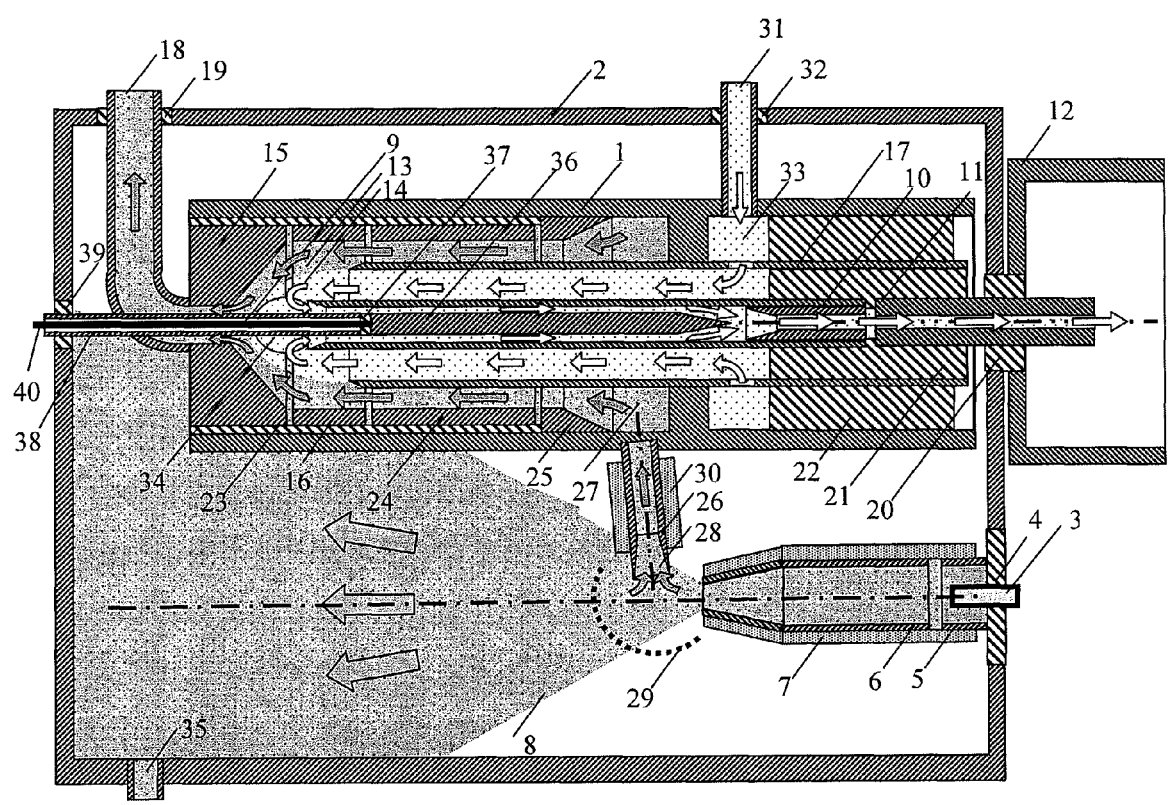
FIG. 2 is a schematic view of a second exemplary, non-limiting embodiment of a "filter for mass- and mobility-analyzers"

A second exemplary embodiment of a "curtain-gas filter" is shown in FIG. 2. This exemplary embodiment is identical to the exemplary embodiment of FIG. 1 except for reference characters 36, 37, 38, 39, 40. Additionally to the electrode arrangements shown in FIG. 1, at least one cylindrical electrode 36 is foreseen placed substantially coaxial within the tube 10 in the exemplary embodiment shown in FIG. 2. This at least one cylindrical electrode 36 is held in place by an insulator 37 and a thin tube 38 which is mounted to the vessel 2 by another insulator 39, wherein a chosen potential is applied via the wire 40 to the at least one cylindrical electrode 36, although any equivalent structure could be used as would be understood by one skilled in the art.

In this exemplary embodiment, gas can flow from the filter volume 9 of the curtain gas filter to the capillary 11 through an annular region between the guide tube 10 and the at least one cylindrical electrode 36 between which constant or varying voltages are applied. The resulting electric fields and the longitudinal gas flow in this annular region then acts as a "differential mobility analyzer (DMA)" as disclosed in E. O. Knutson, K. T. Whitby, J. Aerosol Science 6 (1975) 443, in which ions of high mobilities are pushed to the electrode walls where they are annealed. By varying this potential difference, one may shift the "cutoff threshold" of high-mobility ions.

Adding a high-frequency voltage of an asymmetric waveform between the guide tube 10 and the at least one cylindrical electrode 36, one creates a situation as in a differential mobility FAIMS system" as disclosed in B. M. Kolakowski, Z. Mester, Analyst 132 (2007) 842, in which the nonlinear dependence of the mobility of ions on the magnitude of a deflecting electric field is used to allow at a given time only ions to pass for which the ratio of their high-voltage mobility, and their low-voltage mobility has a determined value. The alternating voltage that has an asymmetric wave form may include a train of substantially rectangular positive and negative voltage pulses that are applied directly between the guide tube 10 and the at least one tubular electrode 36 by a high voltage switch as disclosed in U.S. patent application Ser. No. 11/812,886, having a filing date of Jun. 22, 2007, which is incorporated herein by reference in its entirety. However, the train of substantially rectangular positive and negative voltage pulses may also be applied through a transformer. This will increase the pulse amplitudes but reduce their rectangularity especially for the short pulses which reduces the achievable performance of the mobility analyzer, though a so reduced separation power may still be acceptable for certain applications. For example but not by way of limitation, also an adjustable and/or scanned DC voltage may be added to the train of positive and negative voltage pulses.

This FAIMS-like mobility analysis in the annular region between the guide tube 10 and the at least one cylindrical electrode 36 acts on ions contained in the clean buffer gas. This action may be used instead of or additional to the action of the FAIMS-like mobility analysis in the annular region between the inner tubular electrode 17 and the at least one tube segment 24 that acts on ions contained in the ion-source buffer gas.

Figure 3:
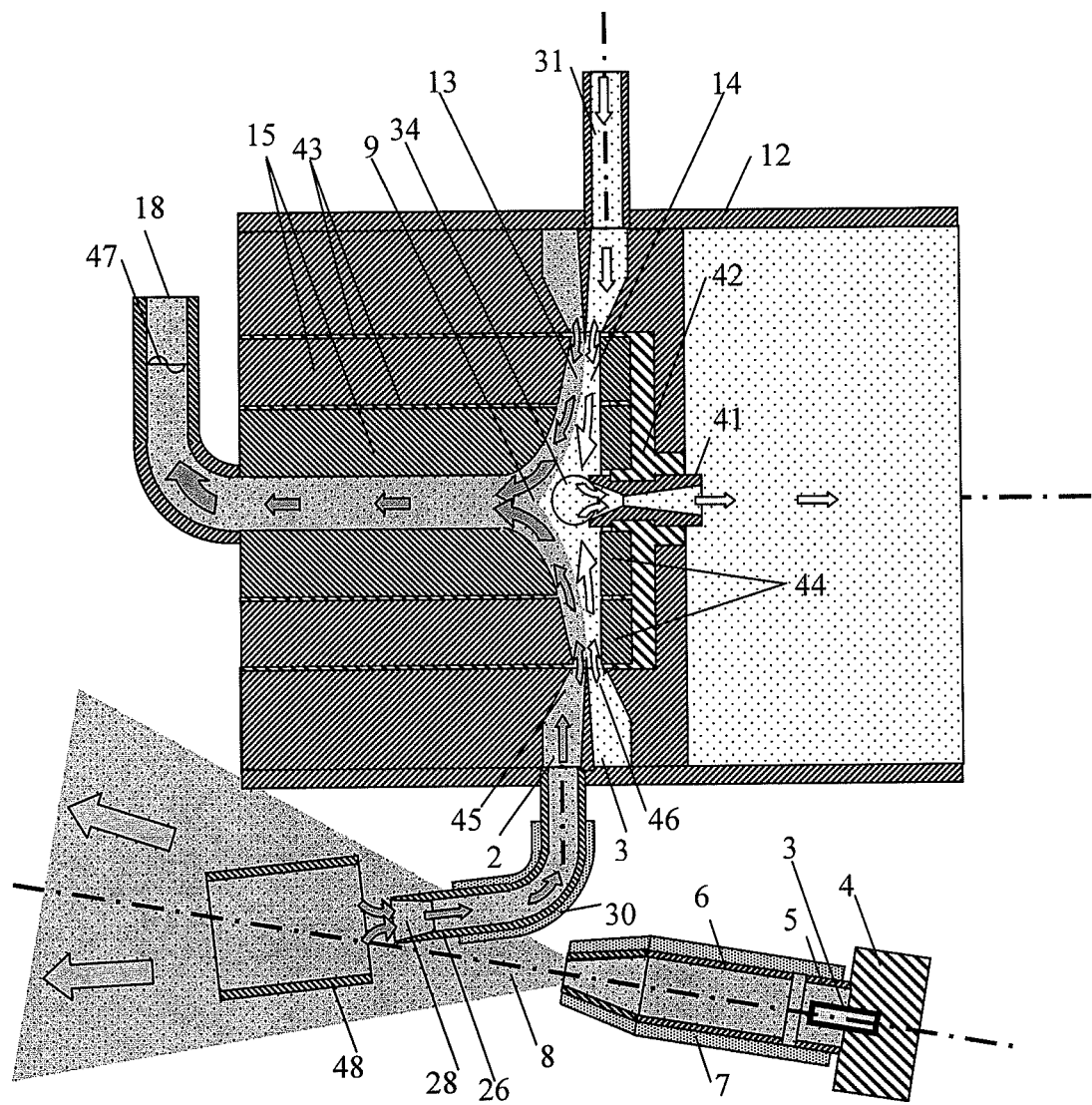
FIG. 3 is a schematic view of a third exemplary, non-limiting embodiment of a "filter for mass- and mobility-analyzers"

FIG. 3 is a schematic view of a third exemplary, non-limiting embodiment of a "curtain-gas filter" for mass- and mobility-analyzers that substantially eliminates ion-source buffer gases and vapors, as well as molecules of very high and very low mobilities and of undesolvated charged droplets. In this exemplary embodiment, the main body of the "curtain-gas filter" is placed at ambient pressure which is also the pressure that exists in the at least one ion-source plume 8 of the "ion-source buffer gas". As in the exemplary embodiments shown in FIG. 1 and in FIG. 2 this at least one ion-source plume 8 originates from at least one ion source 3 and passes through a "desolvation chamber" formed by tubular electrodes 5, 6 and the heater 7. This "desolvation chamber" may enhance the evaporation of the liquid of charged aerosols, whose charges are finally left at individual atoms and molecules originally incorporated in the droplets.

In the exemplary embodiment of FIG. 3, the axis of the at least one ion-source plume 8 may be oblique to the axis of the passage of the curtain-gas filter and also oblique to the axis of the gas intake part 28 of the ion-source buffer-gas inlet 26, though it may as well be substantially parallel or perpendicular.

The ions must be transported from this plume 8 into the main filter volume 9, and from there through a passage, i.e. a short capillary 41, shown in FIG. 3 to be shaped like a Lavall nozzle and into the at least one of a mass-spectrometer and a mobility-spectrometer (both not shown) housed in a low-pressure vessel 12. For this to happen, the "ion-source buffer gas" 13 as well as the externally supplied "clean buffer gas" 14 must be passed radially, i.e. perpendicular to the axis of the capillary 41, into the filter volume 9 as two unmixed gas flows with a common border therebetween. Within this filter volume electric fields push the ions from the flow of the "ion-source buffer gas" 13 into the flow of the "clean buffer gas" 14, i.e. parallel to the axis of the capillary 41 through which the largest part of the "clean buffer gas" with now embedded ions is sucked substantially into the vessel 12.

These electric fields are formed by applying a voltage between the at least one "repeller" 15, which in the exemplary embodiment of FIG. 3 is divided into two substantially conical plungers, and at least one ring electrode 44, which in the exemplary embodiment of FIG. 3 is divided into two substantially concentric ring electrodes held in place by the same insulator 42 that also holds the capillary 41 which extends into the filter volume 9 beyond the at least one ring electrode 44.

The bore of the capillary 41 may have a circular, elliptical or polygonal cross section and is shown in FIG. 3 as to have a form of a Lavall Nozzle in which the bore first decreases and then increases. Further yet the capillary 41 may be built of conductive material or of insulating or high resistivity material with (a) its bore being coated by a conductive layer or by a resistive layer through which a current may be passed or (b) comprise parts made of conductive or of resistive materials through which a current may be passed.

In the exemplary embodiment of a "curtain gas filter" as shown in FIG. 3, there are two gas flows into the main filter volume 9:

A. The flow of the "ion-source buffer gas" 13 is sucked into the filter volume 9 through at least one "ion-source buffer gas inlet" 26 and then through a first low-turbulence gas guide that comprises a ring canal 27, an annular ring slot 45, which also may be chosen to be a number of azimuthally arranged openings, and an annular region formed between the at least one plunger 15 and the at least one ring electrode 44 all formed with very smooth surfaces to keep the gas flow substantially laminar. When the ions in the flow of the "ion-source buffer gas" 13 have been pushed into the flow of the "clean buffer gas" 14 the ion depleted "ion-source buffer gas" is sucked from the filter volume 9 through an exhaust canal 18 by a pump 47 which also ensures that the gas pressure in the filter volume 9 of the "curtain-gas filter" is lower than that in the ion source plume 8. In case the "ion-source buffer gas" in the plume 8 still contains a large number of charged droplets, one may heat the at least one "ion-source buffer gas inlet" 26, for instance by a heater 30, so that the liquid of at least a portion of these droplets evaporates quickly, and the droplet charges are substantially transferred to initially comprised molecules.

B. The flow of the "clean buffer gas" 14 is sucked into the filter volume 9 through at least one "clean buffer gas inlet" 31 and then through a first low-turbulence gas guide that comprises a ring canal 33, an annular ring slot, which also may be chosen to be a number of azimuthally arranged openings, and an annular region formed between the at least one plunger 15 and the at least one ring electrode 44 all built with very smooth surfaces to ensure widely laminar gas flows. When the electric fields in the filter volume 9 have pushed the ions and charged droplets embedded in the "ion-source buffer gas" 13 into the flow of the "clean buffer gas" 14 or directly into the clean buffer gas filled "ion extraction volume" 34, which is that portion of the filter volume 9 from which the main portion of this now ion containing "clean buffer gas" is sucked through the capillary 41, into the vessel 12, while the rest of the "clean buffer gas" is exhausted with the help of the pump 47 through the exhaust canal 18 together with the ion depleted "ion-source buffer gas". For these gas flows to occur, the gas pressure in the plume 8 must be higher than the gas pressure in the main filter volume 9, which in turn must be higher than the pressure in the vessel 12. These pressure differences are established by the pump 47 in the exhaust canal 18, and by limiting the conductances between the ring canals 27 and 33 and the main filter volume 9 of the "curtain-gas filter". To achieve substantially laminar gas flows into and within the filter volume 9 of the "curtain-gas filter" as well as into the capillary 41, the ring slots 45 and 46 are formed so that the gas flow is narrowed before entering the main filter volume 9 of the exemplary embodiment of FIG. 3 of a "curtain-gas filter".

For the same reason, the wall thickness of the at least one "ion-source buffer gas inlet" 26 is thin and may be chamfered at its gas intake part 28. Differently than in the exemplary embodiments shown in FIG. 1 and FIG. 2, in the exemplary embodiment of FIG. 3, the at least one "ion-source buffer-gas inlet" is shown to be curved and arranged so that the gas flow into this "ion-source buffer-gas inlet" is substantially opposite to the gas flow in the plume 8. In the exemplary embodiment shown in FIG. 3 of a "curtain-gas filter" there is also a tubular electrode 48, which may be made from a grid or a solid, to which an ion repelling potential is applied, so that between the tubular electrode 48 and the at least one "ion-source buffer gas inlet" 26 an electric field is formed that pushes ions towards the center of the gas intake part 28 of the "ion-source buffer gas inlet" 26, wherein the axis of the tubular electrode 48 is shown to be substantially coinciding with the axis of the gas intake part 28 of the "ion-source buffer gas inlet".

FIGS. 4, 5, 6, 7 and 8 illustrate exemplary, non-limiting embodiments of electrodes that form an "ion concentrator" arranged around the gas intake part 28 of the "ion-source buffer gas inlet" 26. To the electrodes of these "ion concentrators", potentials are applied that assist the introduction of ions into the "ion-source buffer gas inlet" 26 from the ion-source "plume" 8 by forming potential distributions that approximate one that would be formed, if an ion attracting potential point-charge would be placed at a point 49 substantially in the middle of the gas intake part 28 of the "ion-source buffer gas inlet" 26.

Figure 4:
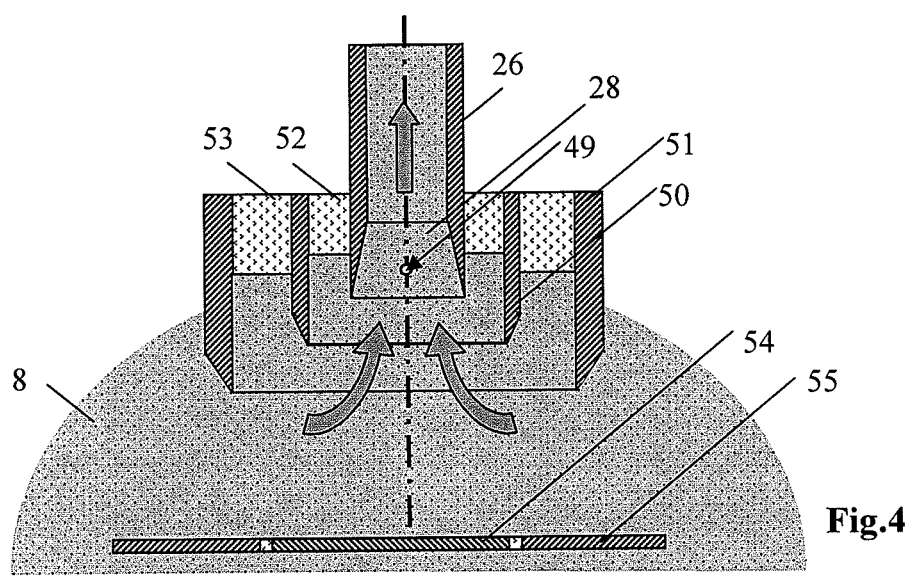
FIG. 4 is a first schematic view of an exemplary, non-limiting embodiment of an ion concentrator arranged in the region around the gas intake part of the "ion-source buffer gas inlet" to a "curtain-gas filter" as shown in FIGS. 1-3.

FIG. 4 shows a first exemplary non-limiting embodiment of an "ion concentrator". Two tubular electrodes 50 and 51 are held in place by tubular insulators 52 and 53 all arranged substantially coaxial around the gas intake entrance part 28 of the at least one "ion-source buffer gas inlet" 26 as well as at least one substantially flat electrode 54, 55 arranged to be substantially parallel to the gas flow of the ion-source plume 8 and as shown in FIG. 4 perpendicular to the axis of the "ion-source buffer gas inlet" 26 and at some distance to the ion-source buffer gas inlet 26.

The potentials applied to the electrodes 50, 51, 54 and 55 here are chosen so that the resulting spatial potential distribution approximates one that would be formed, if an ion attracting potential point charge would be placed at a point 49 substantially in the middle of the gas intake part 28 of the at least one "ion-source buffer gas inlet" 26. However, other similar electrode arrangements are feasible as well. In the exemplary embodiment shown in FIG. 4, the direction of the gas flow of the ion source plume is substantially perpendicular to the drawing plane of FIG. 4, though, in case the electrodes 54, 55 are formed by grids, any other direction may be used, including a direction parallel to the axis of the at least one "ion-source buffer gas inlet" 26 with the gas flow in the "ion-source buffer gas inlet" 26 being substantially antiparallel to the direction of the gas flow in the ion source plume 8.

Figure 5:
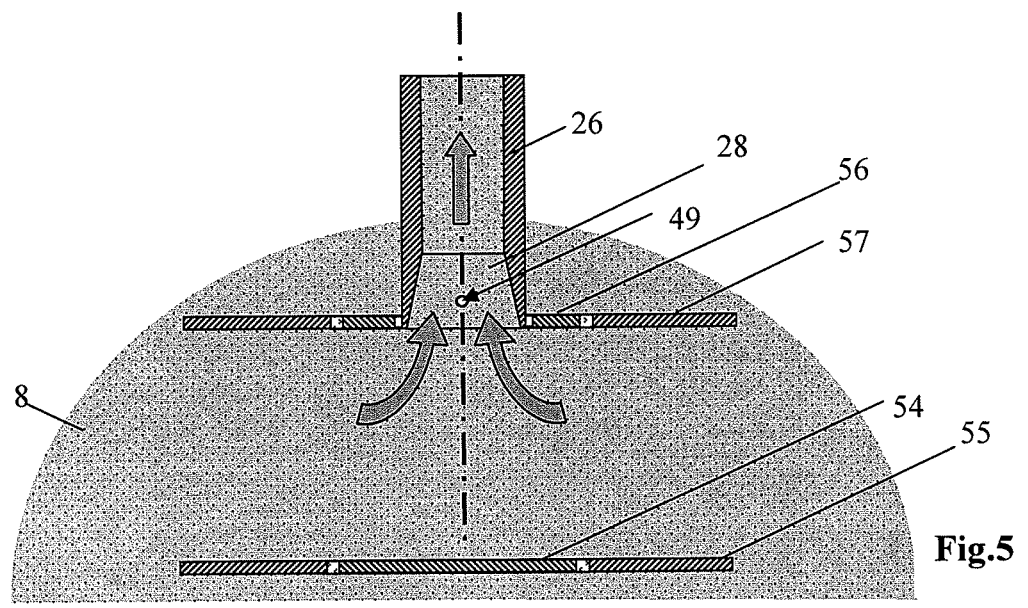
FIG. 5 is a second schematic view of an exemplary, non-limiting embodiment of an ion concentrator arranged in the region around the gas intake part of the "ion-source buffer gas inlet" to a "curtain-gas filter" as shown in FIGS. 1-3.

FIG. 5 shows another exemplary non-limiting embodiment of an "ion concentrator" arranged around the gas intake part 28 of the at least one "ion-source buffer gas inlet" 26. This "ion concentrator" comprises substantially flat electrodes 54, 55, 56, 57 arranged substantially parallel to the gas flow in the ion-source plume and as shown in FIG. 5 perpendicular to the axis of the "ion-source buffer gas inlet" 26, wherein all flat ring electrodes are formed as separate electrodes or as at least one printed circuit board. The potentials of these electrodes are chosen so that the resulting spatial potential distribution approximates one that would be formed, if there would be an ion attracting point charge placed at a point 49 substantially in the middle of the gas intake part 28 of the at least one "ion-source buffer gas inlet" 26. In the exemplary embodiment of FIG. 5, the direction of the gas flow of the ion source plume is substantially perpendicular to the drawing plane of FIG. 5, though, in case the electrodes 54, 55, 56, 57 are formed as grids, any other direction would be feasible, including a direction parallel to the axis of the at least one "ion-source buffer gas inlet" 26 with the gas flow in the at least one "ion-source buffer gas inlet" 26 being substantially antiparallel to the direction of the gas flow in the ion source plume.

Figure 6:
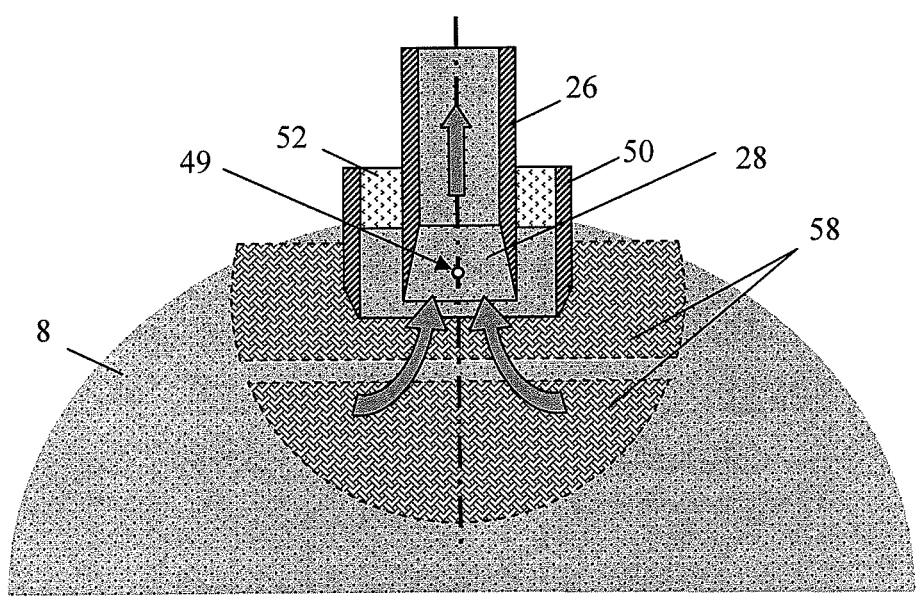
FIG. 6 illustrates an exemplary, non-limiting embodiment of an "ion concentrator" arranged in the region around the gas intake part of the "ion-source buffer gas inlet" to a "curtain-gas filter" as shown in FIGS. 1-3.

FIG. 6 shows yet another exemplary non-limiting embodiment of an "ion concentrator" arranged around the gas intake part 28 of the at least one "ion-source buffer gas inlet" 26. In addition to a tubular electrode 50 held in place by an insulator 52, this "ion concentrator" comprises a grid 58 formed to approximate a sphere whose center is located approximately at a point 49 in the middle of the gas intake part 28 of the at least one "ion-source buffer gas inlet" 26. Though this grid can be formed as a single electrode, it can also be divided into several sections, as is shown in FIG. 6. Applying ion repelling potentials to this grid or these grids, the resulting spatial potential distribution approximates one that would be formed by an ion attracting point charge placed at a point 49 substantially in the middle of the gas intake part 28 of the at least one "ion-source buffer gas inlet" 26. When using this "spherical grid" 58, the ion-source "plume" 8 must pass through the meshes of this grid. However, the gain in ion intensity by the electric forces compensates for these losses.

Figure 7:
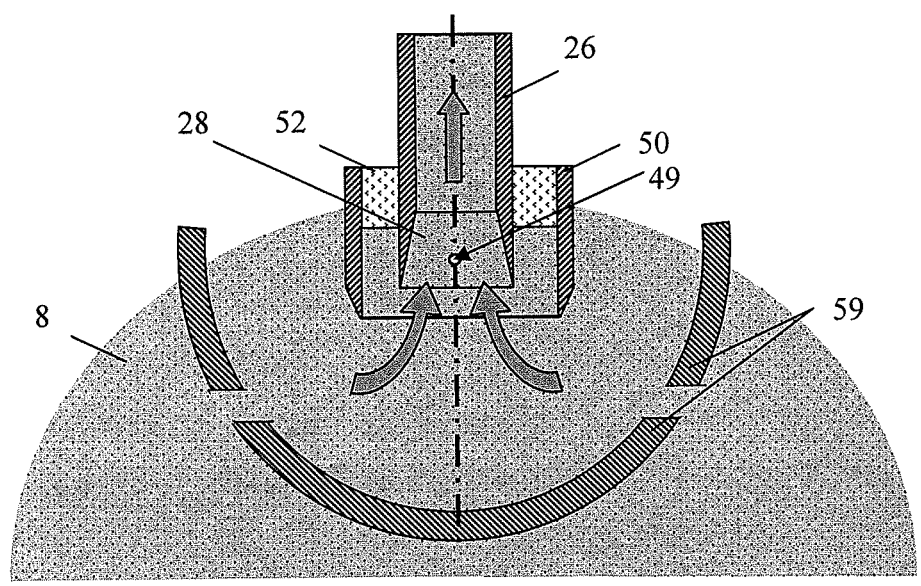
FIG. 7 illustrates an exemplary, non-limiting embodiment of an "ion concentrator" arranged close to the gas intake part of the "ion-source buffer gas inlet" to a "curtain-gas filter" as shown in FIGS. 1-3.

FIG. 7 shows still another exemplary non-limiting embodiment of an "ion concentrator" arranged around the gas intake part 28 of the at least one "ion-source buffer gas inlet" 26. In addition to a tubular electrode 50, held in place by an insulator 52, this "ion concentrator" comprises electrodes 59 formed to approximate at least part of a cylinder whose axis is perpendicular to the drawing plane of FIG. 7 and passes through a point 49 approximately in the middle of the gas intake part 28 of the at least one "ion-source buffer gas inlet" 26. Though electrodes 59 can be formed as a single electrode they can also be divided into several sections as shown in FIG. 7. Applying ion repelling potentials to electrodes 59 a potential distribution is approximated that would be formed if ion attracting potentials would be applied to points along the axis of electrodes 59 formed to approximate at least part of cylinder. Electrodes 59 of the exemplary embodiment shown in FIG. 7 exhibit only forces perpendicular to the cylinder axis, i.e. in the drawing plane and not in a direction perpendicular to this drawing plane of FIG. 7, in contrast to the exemplary embodiment shown in FIG. 6. However, the surfaces of electrodes 59 present no major obstacle to the gas flow in the plume 8 if the axis of this plume is chosen to be parallel to the cylinder axis, i.e. perpendicular to the drawing plane of FIG. 7. The potential distribution formed by the tubular electrode 50, however, add forces that push ions towards the axis of the at least one "ion-source buffer gas inlet" 26.

Figure 8:
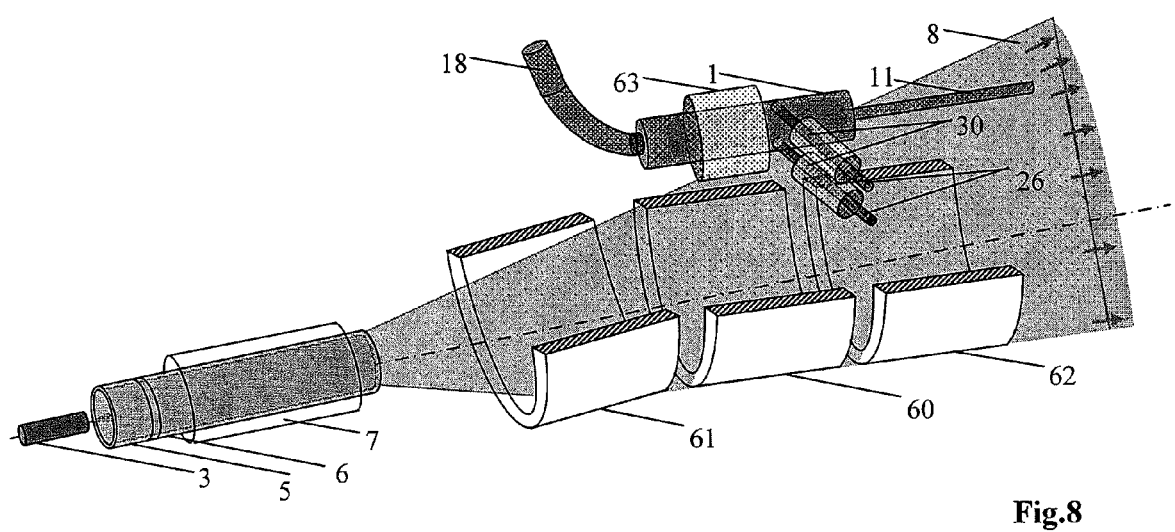
FIG. 8 illustrates a three dimensional view of an exemplary, non-limiting embodiment of an electrode arrangement similar to that of FIG. 7.

FIG. 8 shows a three dimensional view of an exemplary, non-limiting embodiment of an electrode arrangement similar to that of FIG. 7. In this exemplary embodiment, three cylindrical electrodes 60, 61, 62 are shown. Applying different potentials to these cylindrical electrodes 60, 61, 62, the resulting field exhibits onto the ions not only forces that drive them towards the axis of the cylindrical electrodes, but also forces parallel to this axis, so that the ions are better concentrated at the gas intake part 28 of the at least one "ion-source buffer gas inlet" 26. Of these "ion-source buffer gas inlets" two are shown in FIG. 8 which are arranged so that the blow gas approximately tangential into the ring canal 27 as shown more explicitly in FIG. 9. This reduces the gas turbulences in the gas flow within the ring canal 27 so that fewer ions embedded in this gas flow end up at the electrode surfaces within the "curtain-gas filter". In FIG. 8, heaters 30 are shown for the at least one "ion-source buffer gas inlet", as well as a heater 63 for the whole "curtain-gas filter" or at least for the region of the ring canal 27 (not shown in FIG. 8) for the "ion-source buffer gas" within the "curtain-gas filter". The axis of at least one of the cylindrical electrodes—this is shown for the electrode 61—can also be tilted mechanically with respect to the axis of the other electrodes, i.e. the electrodes 60 and 62 in FIG. 8. This allows a slight guiding of the gas flow in the ion-source plume 8. i.e. perpendicular to the axis of the electrodes 60 and 62.

Figure 9:
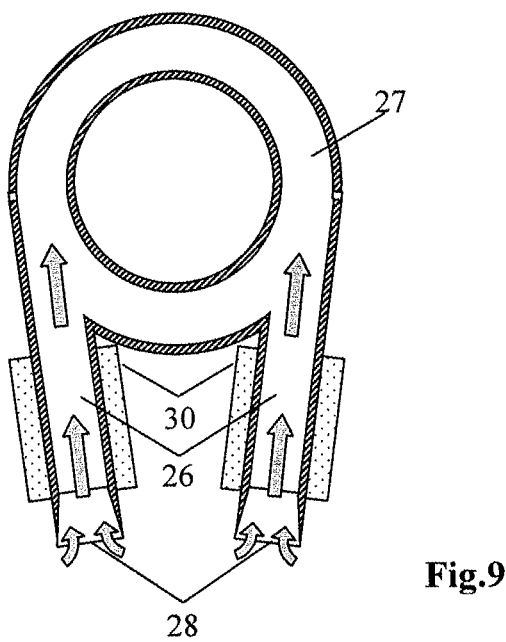
FIG. 9 illustrates an exemplary, non-limiting embodiment in which two "ion-source buffer gas" inlets are arranged so as to blow the "ion-source buffer gas" tangentially into a ring canal of a "filter for mass- and mobility-analyzers".

FIG. 9 shows an arrangement of two "ion-source buffer-gas inlets" which both blow their ion-source buffer gas tangential into the ring canal 27 of the first low-turbulence gas guide, though this tangential connection could also be used for one "ion-source buffer-gas inlet" or for more than two. Such a tangential connection one can not only use for the introduction of "ion-source buffer gases" but as well for "clean buffer gases".

In the exemplary embodiments of a curtain-gas filter shown in FIG. 1 and in FIG. 2 the first and the second low-turbulence gas guide guides gases parallel to their axes which when connected to the ring canal shown in FIG. 9 would be perpendicular to the drawing plane of FIG. 9. The gas flow in the in FIG. 9 shown ring canal thus must move from within the drawing plane of FIG. 9 to a direction perpendicular to this drawing plane which can be achieved (a) if the shown ring canal is part of the annular region of the first or of the second low-turbulence gas guide or (b) if the shown ring canal is connected to the annular region of the first or of the second low-turbulence gas guide by a number of azimuthally arranged openings in the inner wall of the shown ring canal.

In the embodiments of a curtain-gas filter shown in FIG. 3 the first and the second low-turbulence gas guide guides gases perpendicularly to their axes which when connected to the ring canal shown in FIG. 9 would be within the drawing plane of FIG. 9. The gases in the ring canal shown in FIG. 9 thus must move radially through (a) a ring slot which is part of the annular region of the first or of the second low-turbulence gas guide inn FIG. 3 or (b) by an number of azimuthally arranged openings in the inner wall of the in FIG. 9 shown ring canal.

In FIGS. 4-8, the "ion-concentrator" electrodes 50, 51, 54, 55, 56, 57 are shown as being rotationally symmetric around the axis of the gas intake part 28 of the at least one "ion-source buffer gas inlet" 26, though square or rectangular or polygonal electrodes and electrode arrangements could be used as well, as would be understood by those skilled in the art. Furthermore, the electrodes 50, 51, 54, 55, 56, 57 can be divided azimuthally, i.e. with each cut substantially including the axis of the gas intake part 28 of the at least one "ion-source buffer gas inlet" 26. By applying slightly different potentials to these different segments, multipole fields can be formed, including dipole fields, which act substantially perpendicular to the axis of the gas intake part 28 of the at least one "ion-source buffer gas inlet" 26. Thus, the overall ion transmission into the at least one "ion-source buffer gas inlet" 26 can be affected by compensating slightly asymmetric gas-flow forces and/or mechanical misalignments of the gas intake part 28 of the at least one "ion-source buffer gas inlet" 26.

The sections of the "spherical grid" 58 shown in FIG. 6 and the sections of the "cylindrical electrodes" 59 shown in FIG. 7 can be used separately or in combination. The flat electrodes 54, 55 shown in FIGS. 4 and 5 can be replaced by one or by several sections of the "cylindrical electrodes" 59 shown in FIG. 7, or by one or several sections of the "spherical grid" 58 shown in FIG. 6.

In the exemplary embodiments of FIGS. 1-3, high-mobility ions of protonated water clusters and protonated solvent molecules may be substantially eliminated since they would not be incorporated into the clean buffer-gas flow, so that only ions of interest are left in the "ion extraction volume" 34. This allows using the "curtain-gas filter" according to the exemplary embodiments as a monitor of the effluent of a gas- or a liquid-chromatograph as a function of time, if a total ion current detector (not shown) is placed in the spectrometer vessel 12 downstream of the capillary 11 in FIG. 1 or 2, or downstream of the capillary 41 in FIG. 3.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A spectrometry system, comprising:
   an ion source that produces an ion-source plume;
   an ion-source buffer-gas inlet configured to receive ion-source buffer gas from said ion-source plume;
   a clean buffer-gas inlet configured to receive a clean buffer gas from an external source; and
   a curtain-gas filter including,
   at least one first low-turbulence gas guide that transfers said ion-source buffer gas from said ion-source buffer gas inlet to a main filter volume having a gas pressure lower than a gas pressure of said ion-source plume,
   at least one second low-turbulence gas guide that transfers said clean buffer gas from said clean buffer-gas inlet to said main filter volume,
   a passage positioned between an ion extraction volume within the main filter volume and at least one spectrometer having a gas pressure lower than the gas pressure in the main filter volume of said curtain-gas filter, and
   at least two electrodes placed at different potentials to generate an electric field so as to push ions having a range of mobilities from said ion-source buffer gas in said main filter volume into said clean buffer gas in said main filter volume, to generate an ion containing clean buffer gas in an ion extraction volume of said main filter volume,
   wherein the main filter volume includes the ion-source buffer gas and the clean buffer gas as substantially unmixed flows having a boundary therebetween; and
   wherein said ion-containing clean buffer gas in said ion extraction volume flows substantially through said passage into said at least one spectrometer, and any remaining gas in a portion of said main filter volume outside of said ion extraction volume is exhausted.

2. The spectrometry system of claim 1, wherein the ion source is a high-pressure ion source.

3. The spectrometry system of claim 2, wherein the ion source blows its plume into either a region of ambient pressure or a vessel in which the gas pressure is between approximately 20 mbar and several bar.

4. The spectrometry system of claim 1, wherein said ion-source plume comprises embedded ions.

5. The spectrometry system of claim 1, wherein said at least one spectrometer comprises at least one of a mass spectrometer and a mobility spectrometer.

6. The spectrometry system of claim 1, wherein an end of said passage is either substantially flush with or extends deeper into the main filter volume beyond an inner tubular electrode or an outer tubular electrode both arranged substantially coaxial around said passage or at least one flat ring electrode surrounding the end of said passage.

7. The spectrometry system of claim 6, wherein at least one of said inner tubular electrode, said outer tubular electrode and said at least one surrounding flat ring electrode is divided into at least two parts to which different potentials are applied.

8. The spectrometry system of claim 7, wherein said inner tubular electrode, said outer tubular electrode and said at least one surrounding flat ring electrode is divided azimuthally or longitudinally.

9. The spectrometry system of claim 6, wherein said passage itself and/or at least one of said inner tubular electrode or said outer tubular electrode and/or at least one of said at least one surrounding flat ring electrode are replaced by at least two substantially planar electrodes that are either substantially parallel to the axis of said passage or that are substantially symmetric and inclined relative to the axis of said passage and wherein different potentials may be applied to said at least two substantially flat plates.

10. The spectrometry system of claim 6, wherein the main filter volume of said curtain-gas filter is defined on one side by the end of said passage and by the end of said inner tubular electrode as well as the end of said outer tubular electrode, and is defined on the other side by at least one repeller electrode whose axis is parallel to or coinciding with the axis of said passage wherein said electric field in the main filter volume is formed by applying to said at least one repeller equal or different ion repelling potentials measured relative to the potential of the gas intake part of said passage and/or by applying to the inner tubular electrode and/or to the outer tubular electrode the same or different potentials than to said passage.

11. The spectrometry system of claim 10, wherein a tubular ring electrode is arranged substantially proximal to said repeller and placed substantially around the main filter volume with the axis of the tubular ring electrode being parallel to or coinciding with the axis of said passage wherein said ring electrode may be subdivided into at least two sections and wherein to these subelectrodes equal or different ion repelling potentials may be applied.

12. The spectrometry system of claim 6, wherein the inner tubular electrode is made of very thin material which additionally may be chamfered at the inside and the outside, and both surfaces of said inner tubular electrode as well as the inner surface of said outer tubular electrode and the outer surface of said passage are very smooth.

13. The spectrometry system of claim 6, wherein a static and/or an alternating voltage is applied between the inner tubular electrode and a section of the outer tubular electrode.

14. The spectrometry system of claim 1, in which said passage comprises at least one of a capillary and a diaphragm of circular, elliptical or polygonal bore that guides said ion containing clean buffer gas from said ion extraction volume into said at least one spectrometer.

15. The spectrometry system of claim 14, in which said passage further comprises at least one guide tube of circular, elliptical or polygonal bore that transports said ion-containing clean buffer gas from said ion extraction volume, through said at least one of said capillary and said diaphragm, and into said at least one spectrometer wherein different potentials may be applied to said at least one guide tube as compared with said at least one of said capillary and said diaphragm.

16. The spectrometry system of claim 15, wherein the bores of said at least one capillary, said at least one guide tube and said inner tubular electrode and said outer tubular electrode have cross sections that are constant or varied over parts of their respective lengths.

17. The spectrometry system of claim 15, wherein said at least one capillary is shaped to have a form of a Lavall Nozzle.

18. The spectrometry system of claim 1, in which said at least one first low-turbulence gas guide and said at least one second low-turbulence gas guide each comprise at least one ring canal and at least one annular region formed (a) between said passage and said inner tubular electrode, and (b) between said inner tubular electrode and an outer tubular electrode, wherein the cross sections of the respective annular regions are constant or are varied for at least part of their length.

19. The spectrometry system of claim 18, wherein said ion-source buffer-gas and said clean buffer-gas each flow from the at least one ring canal either directly or via at least one aperture through respective annular regions of said first low-turbulence gas guide and of said second low-turbulence gas guide substantially parallel to the axis of said passage, and opposite to the gas flow direction in said passage.

20. The spectrometry system of claim 18, wherein said passage comprises an insulating or highly resistive material having (a) an inner surface coated by a conductive or of a resistive material or (b) parts made of conductive or of resistive materials.

21. The spectrometry system of claim 18, comprising at least one substantially cylindrical electrode placed within said at least one guide tube of said passage so as to permit application of a static and/or alternating voltage therebetween, wherein axes of said at least one guide tube and said at least one substantially cylindrical electrode are parallel or coinciding.

22. The spectrometry system of claim 21, wherein said alternating voltage is a high frequency voltage that has an asymmetric wave form comprising a train of substantially rectangular positive and negative pulses with the positive pulses having different amplitudes and durations than the negative pulses and wherein an absolute value of an integral over the positive pulses is substantially equal to an absolute value of an integral over the negative pulses.

23. The spectrometry system of claim 22, wherein an adjustable and/or scanned DC voltage is added to said train of positive and negative pulses.

24. The spectrometry system of claim 22, wherein said train is generated by a high voltage switch and applied directly to said at least one substantially cylindrical electrode.

25. The spectrometry system of claim 22, wherein said train is generated by a high voltage switch and applied to said at least one substantially cylindrical electrode through a transformer.

26. The spectrometry system of claim 1, in which said first low-turbulence gas guide and said second low-turbulence gas guide each comprise at least one ring canal and at least one annular region that is formed between plates arranged parallel to the respective planes of said ring canals wherein the ion-source buffer-gas and the clean buffer-gas flow radially between said plates to said passage, wherein an axis of said passage is substantially perpendicular to the planes of said ring canals.

27. The spectrometry system of claim 1, wherein said at least one ion-source buffer gas inlet and/or said at least one clean buffer gas inlet is arranged substantially radial or substantially tangential to respective ring canals into which the ion-source buffer gas or the clean buffer gas is guided.

28. The spectrometry system of claim 27, wherein said ion-source buffer gas ring canal and/or said clean buffer gas ring canal is either part of said respective annular region or is connected to said respective annular region by a number of azimuthally arranged openings in at least one of the ring canals or tubular electrodes that form said annular region.

29. The spectrometry system of claim 1, wherein said curtain-gas filter is mounted in a vessel into which the ion source sends the ion-source plume at an elevated gas pressure maintained by controlling the gas pressure of the ion source, and wherein the gas pressure of the external clean buffer gas supply is adjusted so that the clean buffer gas flow into the main filter volume of the curtain-gas filter exceeds the flow from the main filter volume through said passage.

30. The spectrometry system of claim 1, wherein the gas pressure in said ion-source plume is at ambient pressure and a pump reduces the gas pressure in the main filter volume to a gas pressure that is lower than the pressure in said ion-source plume, wherein said pump exhausts gas from said main filter volume, and wherein the pressure of the external clean buffer gas supply is adjusted so that the clean buffer gas flow into the main filter volume of the curtain-gas filter exceeds the flow from the main filter volume through said passage.

31. The spectrometry system of claim 1, wherein the bore of at least one of said at least one ion-source buffer gas inlet is heated and of substantially round, elliptical or polygonal cross section and increases or decreases its diameter for at least a portion of its length and wherein the wall of the intake part of the ion-source buffer-gas inlet is very thin and chamfered at at least one its inside and its outside.

32. The spectrometry system of claim 1, wherein at least one ion concentrator is arranged around and/or at some distance to a gas intake part of said ion-source buffer gas inlet.

33. The spectrometry system of claim 32, wherein the axis of said at least one tubular electrode is substantially parallel to or coincides with the axis of the gas intake part of said ion-source buffer gas inlet and wherein the ion concentrator is made of conductive or low resistive gridded or solid material with ion repelling potentials being applied to the ion concentrator so that the formed electric field approximates that which would be obtained by an ion attracting point-charge placed approximately in the middle of the gas intake part of the ion-source buffer gas inlet, and wherein said ion concentrator comprises one of (a) a tubular electrode or circular, elliptical, or polygonal cross-section, (b) at least one planar ring electrode of circular, elliptical or polygonal area, (c) at least one grid that approximates a sphere whose center is located approximately in the middle of the gas intake part of said at least one ion-source buffer gas inlet wherein an ion repelling potential is applied to said at least one spherical grid, and (d) at least one electrode that approximates the form of a half-cylinder whose axes pass substantially through a point located approximately in the middle of the gas intake part of the at least one ion-source buffer gas inlet.

34. The spectrometry system of claim 33, wherein said ion concentrator is divided into at least two parts.

35. The spectrometry system of claim 33, wherein the axis of said planar ring electrode is not parallel to the axis of the at least one ion-source buffer gas inlet, and is inclined at an angle of inclination such that the plane of the planar ring electrode is substantially parallel to the axis of the ion source plume.

36. The spectrometry system of claim 33, wherein said at least one planar ring electrode is formed as a printed circuit board.

37. The spectrometry system of claim 33, wherein the axis of at least one of said at least one electrode that approximates the form of a half-cylinder is tilted with respect to the axes of other electrodes that approximate the form of a half-cylinder.

38. The spectrometry system of claim 1, wherein at least one ion extracting and beam forming electrode of round, elliptical or polygonal cross section is arranged around a part of the at least one ion source plume and placed at different potentials than that of the ion source, wherein the axis of the ion extracting and beam forming electrode is straight or curved.

39. The spectrometry system of claim 38, wherein the ion extracting and beam forming electrode is split into at least two parts to which equal or different potentials DC- and/or AC-potentials are applied.

40. The spectrometry system of claim 38, wherein one of the at least one ion extracting and beam forming electrodes closest to the ion source is at a potential close to that of the ion source.

41. The spectrometry system of claim 38, wherein said at least one ion extracting and beam forming electrode is heated.

42. The spectrometry system of claim 1, wherein at least one of a purity, a pressure, a temperature, and a humidity of said externally supplied clean buffer gas or said ion-source buffer gas in said ion-source plume is controlled, kept constant or varied over time.

43. The spectrometry system of claim 1, wherein to the clean buffer gas a shift reagent is added which either reacts chemically with mobility selected molecule ions or that becomes at least one adduct to said mobility selected molecule ions so that the resulting ion has a different mass than the original molecule ion.

44. The spectrometry system of claim 43, wherein said shift reagent is added intermittently for short periods, so that said molecules of larger or smaller masses or of larger or smaller mobilities appear only for short periods in the recorded spectra of said at least one spectrometer.

* * * * *